(12) United States Patent (10) Patent No.: US 8,361,991 B2
Marat (45) Date of Patent: Jan. 29, 2013

(54) HYDROXYLATED AMIDE SKIN MOISTURIZER

(75) Inventor: Xavier Marat, Paris (FR)

(73) Assignee: L'Oreal, Paris (FR)

( * ) Notice: Subject to any disclaimer, the term of this patent is extended or adjusted under 35 U.S.C. 154(b) by 797 days.

(21) Appl. No.: 12/302,398

(22) PCT Filed: May 3, 2007

(86) PCT No.: PCT/EP2007/054278
§ 371 (c)(1), (2), (4) Date: Sep. 24, 2009

(87) PCT Pub. No.: WO2007/137925
PCT Pub. Date: Dec. 6, 2007

(65) Prior Publication Data
US 2010/0009933 A1 Jan. 14, 2010

Related U.S. Application Data

(60) Provisional application No. 60/811,094, filed on Jun. 6, 2006.

(30) Foreign Application Priority Data

May 31, 2006 (FR) ..................... 06 51987

(51) Int. Cl.
*A61K 8/42* (2006.01)
(52) U.S. Cl. ........... 514/63; 514/423; 514/551; 514/625
(58) Field of Classification Search ..................... 514/63
See application file for complete search history.

(56) References Cited

FOREIGN PATENT DOCUMENTS
FR 2 874 610 3/2006

OTHER PUBLICATIONS

Registry 60094-76-0 registered on Nov. 16, 1984.*
Stamatis et al (In vitro inhibition of *Helicobacter pylori* by micromycetes. FEMS Immunology & Medical Microbiology, 45: 71-74 (2005)).*
Wilkin et al (Standard classification of rosacea: Report of the National Rosacea Society Expert Committee on the Classification and Staging of Rosacea. J Am Acad Dermatol 2002; 46:584-7).*
Del Rosso (Medical treatment fo rosacea with emphasis on topical therapies. Expert Opin. Pharmacother. (2004) 5(1):5-13).*

* cited by examiner

*Primary Examiner* — Jake M. Vu
(74) *Attorney, Agent, or Firm* — Oblon, Spivak, McClelland, Maier & Neustadt, L.L.P.

(57) ABSTRACT

The invention relates to the cosmetic use, as a skin moisturizer, of a compound of formula (I): with (i) $R^1$ and $R^2$ represent a hydrogen atom or a $C_1$-$C_6$-alkyl group, or (ii) $R^1$ and $R^2$ can form, together with the nitrogen atom which bears them, a saturated heterocycle with 5 to 7 ring members; $R^5$ representing a hydrogen atom or a ($C_1$-$C_3$) alkyl group; $R^6$ representing a hydrogen atom or a ($C_1$-$C_4$) alkyl group; $R^3$ represents a hydrogen atom or a ($C_1$-$C_6$) alkyl-group, or —$OR^3$ represents a phosphate group; it being possible for the two groups $R^3$ to form, together, an isopropylidene group; $R^4$ represents a hydrogen atom or —$OR^4$ represents a-phosphate group; and the salts, solvates and isomers thereof. The invention also relates to a cosmetic composition comprising a compound (I) and the corresponding new compounds.

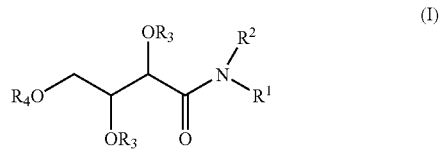

(I)

20 Claims, No Drawings

HYDROXYLATED AMIDE SKIN MOISTURIZER

This application is a National Stage of PCT/EP07/54278 filed May 3, 2007 and claims the benefit of U.S. 60/811,094 filed Jun. 6, 2006 and FR06/51987 filed May 31, 2006.

The present invention relates to the use of specific amides in the skincare field, and in particular as a skin moisturizer, novel urea derivatives and also the cosmetic or dermatological compositions contained therein.

The Stratum Corneum, which forms the interface with the dehydrating external environment, serves in particular to retard the excessive water loss from the deeper layers of the epidermis. The Stratum Corneum also protects against mechanical attack and the passage of chemical products and foreign microorganisms. It also constitutes the first line of defence against UV radiation.

The Stratum Corneum, which is 10 μm thick, is composed of vertically stacked corneocytes surrounded by a matrix of lipid-enriched membranes. Thus, it is a two-compartment system that may be compared to a brick wall, composed of anuclear cells (the "bricks") and of intercellular lamellar membranes (the "cement").

Urea is one of the ingredients widely used in moisturizing formulations. However, it can greatly modify the skin barrier by increasing the transepidermal water loss (TWL), which significantly reduces the barrier function of the Stratum Corneum.

Glycerol, another reference active agent in this field, has the drawback of making the formulations tacky when it is used at high concentration.

There is thus a need to find alternative solutions in the field of skin moisturization.

The inventors have discovered that certain amides of general formula (I) described below are good moisturizers and have a beneficial effect in terms of elasticity of the Stratum Corneum.

Thus, a subject of the present invention is the cosmetic use, as a skin moisturizer, of the compounds of general formula (I):

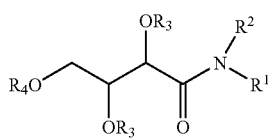

in which
(i) $R^1$ and $R^2$ represent, independently of one another, a hydrogen atom, or a saturated $C_1$-$C_6$ or unsaturated $C_2$-$C_6$ linear alkyl group or saturated or unsaturated $C_3$-$C_6$ branched alkyl group, optionally substituted with one or more groups, which may be identical or different, chosen from —$OR^5$, —$SiMe_3$, —$CO_2R^6$ and —F; or
(ii) $R^1$ and $R^2$ can form, together with the nitrogen atom which bears them, a saturated heterocycle with 5 to 7 ring members, and optionally comprising another heteroatom chosen from sulphur and oxygen (this heterocycle being chosen in particular from pyrrolidine, piperidine, morpholine, thiomorpholine and cyclohexamethylene-imine (or homopiperidine), and preferably pyrrolidone), this heterocycle being optionally substituted with 1 to 3 (preferably 1) linear ($C_1$-$C_4$) or branched ($C_3$-$C_4$) alkyl group(s) optionally substituted with one or more OH groups;

$R^5$ representing a hydrogen atom, or a linear ($C_1$-$C_3$) or branched $C_3$ saturated, or ($C_2$-$C_3$) unsaturated alkyl group;

$R^6$ representing a hydrogen atom or a linear ($C_1$-$C_4$) or branched ($C_3$-$C_4$) saturated alkyl group;

$R^3$ represents a hydrogen atom or a linear ($C_1$-$C_6$) saturated alkyl group, or —$OR^3$ represents a phosphate group; it being possible for the two groups $R^3$ to form, together, an isopropylidene group;

$R^4$ represents a hydrogen atom or —$OR^4$ represents a phosphate group;

and the salts, isomers and solvates thereof.

Some compounds of formula (I) are known:

(2R,3R)-4-Amino-2,3-dihydroxy-4-oxobutyl dihydrogen phosphate (compound 1 mentioned hereinafter) is described in the article C Dardonville et al., "Selective inhibition of *Trypanosoma brucei* 6-phospho-gluconate dehydrogenase by high-energy intermediate and transition-state analogues"; Journal of Medicinal Chemistry, 2004, 47, 13, 3427-3437.

(2R,3R)-2,3,4-Trihydroxy-N,N-dimethylbutanamide (compound 2 mentioned hereinafter) is described in the articles T Woodhall et al., "Synthesis of screening substrates for the directed evolution of sialic acid aldolase: towards tailored enzymes for the preparation of influenza A sialidase analogues"; Organic and Biomolecular Chemistry, 2005, 3, 9, 1795-1800; and Carreira E et al., "Synthesis of (+)-zaragozic acid C"; Journal of the American Chemical Society, 1994, 116, 23, 10825-10826.

(2R,3R)-2,3,4-Trihydroxy-N,N-dipropylbutanamide and (4R,5R)-5-(hydroxymethyl)-2,2-dimethyl-N,N-dipropyl-1,3-dioxolane-4-carboxamide are described in the article by Woodhall T et al., "Synthesis of screening substrates for the directed evolution of sialic acid aldolase: towards tailored enzymes for the preparation of influenza A sialidase analogues"; Organic and Biomolecular Chemistry, 2005, 3, 9, 1795-1800.

(2R,3R)-2,3,4-Trihydroxybutanamide (compound 3 mentioned hereinafter) is described in the article MacDonald et al., "The synthesis of D-erythro-pentulose tetrabenzoate"; Journal of the American Chemical Society, 1958, 80, 3379-3381.

Methyl [(2,3,4-trihydroxybutanoyl)amino]acetate (compound 16 mentioned hereinafter) is described in the article Vertiev, Yu et al., "Characteristics of the enzymic properties of neuraminidase from diphtheria microbes" Editor(s): Rasskazov, V. A. Tezisy Dokl.-Vses. Simp. Bioorg. Khim. (1975), 49.

(2R,3R)-4-Amino-2,3-dihydroxy-4-oxobutyl disodium phosphate (compound 17 mentioned hereinafter) is described in the article Burgos, Emmanuel et al; "Synthesis and evaluation of new 4-phospho-D-erythronic acid derivatives as competitive inhibitors of spinach ribose-5-phosphate isomerase"; Tetrahedron Letters (2004), 45(4), 753-756 (compound 3).

(2R,3S)-2,3,4-Trihydroxybutanamide (compound 18 mentioned hereinafter) is described in the article Wei, Chung Chen et al; "Synthesis of chiral β-lactams using L-ascorbic acid"; Journal of Organic Chemistry (1985), 50(19), 3462-3467 (compound 12), and in application EP-A-0111326 (compound XXVIII; example 4).

(2S,3R)-2,3,4-Trihydroxybutanamide (compound 19 mentioned hereinafter) is referenced under CAS No. 74464-43-0.

(2R,3S)-4-Amino-2,3-dihydroxy-4-oxobutyl disodium phosphate (compound 20 mentioned hereinafter) is described in the article Phaosiri, Chanokporn et al.; "Substrate analogs for the investigation of deoxyxylulose 5-phosphate reductoisomerase inhibition; synthesis and evaluation"; J. Bioorganic & Medicinal Chemistry Letters (2004), 14(21), 5309-5312 (compound 12).

(2R,3S)-4-Amino-2,3-dihydroxy-4-oxobutyl dihydrogen phosphate (compound 21 described hereinafter) is described in the article Walker, Joel R. et al.; "Synthesis and Evaluation of 1-Deoxy-D-xylulose 5-Phosphate Analogs as Chelation-Based Inhibitors of Methylerythritol Phosphate Synthase"; Journal of Organic Chemistry (2005), 70(24), 9955-9959 (compound 4).

(2S,3S)-2,3,4-Trihydroxybutanamide (compound 22 described hereinafter) is the I-erythreonamide compound described in the article Glattfeld, J. W. E. et al.; "Preparation of aldonic and saccharinic acid amides in liquid ammonia"; Journal of the American Chemical Society (1934), 56 2481-2.

Compounds of formula (I) for which $R^1=R^3=R^4=H$ and $R^2$ denotes a $C_8$-$C_{24}$ alkyl group are described in U.S. Pat. No. 5,352,386 as surfactants in detergent cosmetic compositions.

Another subject of the present invention is a composition, in particular a cosmetic or dermatological composition, comprising, in a physiologically acceptable medium, a compound of formula (II) below:

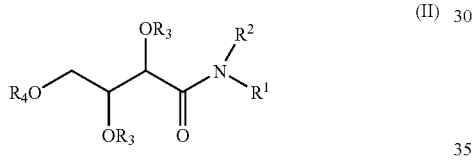

(II)

in which
(i) $R^1$ and $R^2$ represent a hydrogen atom, or
(ii) $R^1$ represents a hydrogen atom and $R^2$ represents a saturated $C_1$-$C_6$ or unsaturated $C_2$-$C_6$ linear alkyl group or saturated or unsaturated $C_3$-$C_6$ branched alkyl group, substituted with one or more groups, which may be identical or different, chosen from —OH, —SiMe$_3$, —CO$_2$R$^6$ and —F;
or
(iii) $R^1$ and $R^2$ represent a saturated $C_1$-$C_6$ or unsaturated $C_2$-$C_6$ linear alkyl group or saturated or unsaturated $C_3$-$C_6$ branched alkyl group, optionally substituted with one or more groups, which may be identical or different, chosen from —OR$^5$, —SiMe$^3$, —CO$_2$R$^6$ and —F;
or
(iv) $R^1$ and $R^2$ form, together with the nitrogen atom which bears them, a saturated heterocycle with 5 to 7 ring members and optionally comprising another heteroatom chosen from sulphur and oxygen, this heterocycle being optionally substituted with 1 to 3 (preferably 1) linear ($C_1$-$C_4$) or branched ($C_3$-$C_4$) alkyl group(s) optionally substituted with one or more OH groups;

$R^5$ representing a hydrogen atom, or a linear ($C_1$-$C_3$) or branched $C_3$ saturated, or ($C_2$-$C_3$) unsaturated alkyl group;

$R^6$ representing a hydrogen atom or a linear ($C_1$-$C_4$) or branched ($C_3$-$C_4$) saturated alkyl group;

$R^3$ represents a hydrogen atom or a linear ($C_1$-$C_6$) saturated alkyl group, or —OR$^3$ represents a phosphate group; it being possible for the two groups $R^3$ to form, together, an isopropylidene group;

$R^4$ represents a hydrogen atom or —OR$^4$ represents a phosphate group;

and the salts, isomers and solvates thereof.

The composition according to the invention preferably contains a cosmetic ingredient chosen from oils, waxes, thickeners, film-forming polymers, preserving agents, fragrances, fillers, UV-screening agents, bactericides, odour absorbers, dyestuffs, cosmetic active agents, plant extracts, antioxidants and surfactants.

A subject of the present invention is also a cosmetic treatment process for non-therapeutic skincare and/or for making up the skin, characterized in that it comprises the application to the skin of a cosmetic composition comprising, in a physiologically acceptable medium, a compound of formula (II) as defined above.

A subject of the invention is also the new compounds of formula (III):

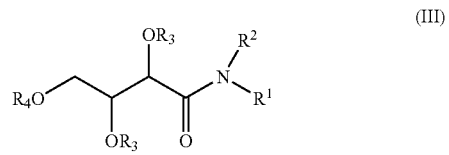

(III)

in which:
(i) $R^1$ represents a hydrogen atom and $R^2$ represents a saturated $C_1$-$C_6$ or unsaturated $C_2$-$C_6$ linear alkyl group or saturated or unsaturated $C_3$-$C_6$ branched alkyl group, substituted with one or more groups, which may be identical or different, chosen from —OH, —SiMe$_3$, —CO$_2$R$^6$ and —F, $R^2$ not denoting a —CH$_2$—CO—O—CH$_3$ group;
or
(ii) $R^1$ and $R^2$ represent a saturated $C_2$ or $C_4$-$C_6$ or unsaturated $C_2$-$C_6$ linear, or saturated or unsaturated $C_3$-$C_6$ branched alkyl group, which is unsubstituted;
or
(iii) $R^1$ and $R^2$ represent a saturated $C_1$-$C_6$ or unsaturated $C_2$-$C_6$ linear, or saturated or unsaturated $C_3$-$C_6$ branched alkyl group, substituted with one or more groups, which may be identical or different, chosen from —OR$^5$, —SiMe$_3$, —CO$_2$R$^6$ and —F;
or
(iv) $R^1$ and $R^2$ form, together with the nitrogen atom which bears them, a saturated heterocycle with 5 to 7 ring members and optionally comprising another heteroatom chosen from sulphur and oxygen, this heterocycle being optionally substituted with 1 to 3 (preferably 1) linear ($C_1$-$C_4$) or branched ($C_3$-$C_4$) alkyl group(s) optionally substituted with one or more OH groups;

$R^5$ representing hydrogen, or a linear ($C_1$-$C_3$) or branched $C_3$ saturated, or ($C_2$-$C_3$) unsaturated alkyl group;

$R^6$ representing a hydrogen atom or a linear ($C_1$-$C_4$) or branched ($C_3$-$C_4$) saturated alkyl group;

$R^3$ represents a hydrogen atom or a linear ($C_1$-$C_6$) saturated alkyl group, or —OR$^3$ represents a phosphate group; it being possible for the two groups $R^3$ to form, together, an isopropylidene group;

$R^4$ represents a hydrogen atom or —OR$^4$ represents a phosphate group;

and the salts, isomers and solvates thereof.

Advantageously, the compounds of formulae (I), (II) and (III) described above have the following stereochemistry:

$$R_4O\underset{\overline{O}R_3}{\overset{OR_3}{\underset{(R)}{\overset{(R)}{\diagdown}}}}\underset{O}{\overset{R^{2'}}{\diagdown}}N_{R^{1'}}$$

In the context of the present invention, the term "alkyl" signifies a linear or branched, saturated or unsaturated, cyclic or noncyclic hydrocarbon-based chain. Among alkyl groups that are suitable for the implementation of the invention, mention may in particular be made of the methyl, ethyl, isopropyl, n-propyl, n-butyl, t-butyl, —CH$_2$-t-butyl, pentyl, n-hexyl, cyclopropyl, cyclopentyl, cyclohexyl, cyclohexylmethyl, heptyl, octyl, nonyl, decyl, undecyl, dodecyl, norbornyl and adamantyl group.

The acceptable salts for the non-therapeutic use of the compounds described in the present invention include conventional non-toxic salts of said compounds such as those formed from organic or inorganic acids. By way of example, mention may be made of the salts of inorganic acids, such as sulphuric acid, hydrochloric acid, hydrobromic acid, hydriodic acid, phosphoric acid or boric acid. Mention may also be made of the salts of organic acids, which may comprise one or more carboxylic, sulphonic or phosphonic acid groups. They may be linear, branched or cyclic aliphatic acids or alternatively aromatic acids. These acids may also comprise one or more heteroatoms chosen from O and N, for example in the form of hydroxyl groups. Mention may in particular be made of propionic acid, acetic acid, terephthalic acid, citric acid and tartaric acid.

When the compound of formula (I), (II) or (III) comprises an acid group, the neutralization of the acid group(s) can be carried out with an inorganic base, such as LiOH, NaOH, KOH, Ca(OH)$_2$, NH$_4$OH, Mg(OH)$_2$ or Zn(OH)$_2$; or with an organic base such as a primary, secondary or tertiary alkylamine, for example triethylamine or butylamine. This primary, secondary or tertiary alkylamine may comprise one or more nitrogen and/or oxygen atoms and may therefore comprise, for example, one or more alcohol functions; mention may in particular be made of 2-amino-2-methylpropanol, triethanolamine, 2-dimethylaminopropanol and 2-amino-2-(hydroxymethyl)-1,3-propanediol. Mention may also be made of lysine or 3-(dimethylamino)propylamine.

The acceptable solvates for the non-therapeutic use of the compounds described in the present invention include conventional solvates such as those formed in the final step of preparation of said compounds due to the presence of solvents. By way of example, mention may be made of the solvates due to the presence of water or of linear or branched alcohols, such as ethanol or isopropanol.

The preferred compounds of formula (I) are those for which:
(i) $R^1$ and $R^2$ represent, independently of one another, a hydrogen atom, or a linear $C_1$-$C_6$ or branched $C_3$-$C_6$ saturated alkyl group optionally substituted with one or more groups, which may be identical or different, chosen from —OH, —SiMe$_3$, —CO$_2$R$^6$ and —F; or
(ii) $R^1$ and $R^2$ can form, together with the nitrogen atom which bears them, a saturated heterocycle with 5 to 7 ring members and optionally comprising another heteroatom chosen from sulphur and oxygen (this heterocycle being chosen in particular from pyrrolidine, piperidine, morpholine, thio-morpholine and cyclohexamethyleneimine (or homopiperidine), and preferably pyrrolidine, this heterocycle being optionally substituted with 1 to 3 (preferably 1) linear ($C_1$-$C_4$) or branched ($C_3$-$C_4$) alkyl group(s) optionally substituted with one or more OH groups;
$R^6$ representing a hydrogen atom or a linear ($C_1$-$C_4$) or branched ($C_3$-$C_4$) saturated alkyl group;
$R^3$ represents a hydrogen atom;
$R^4$ represents a hydrogen atom or —OR$^4$ represents a phosphate group.

Preferably, use is made of compounds of formula (I) for which:
(i) $R^1$ and $R^2$ represent, independently of one another, a hydrogen atom, or a linear $C_1$-$C_4$ or branched $C_3$-$C_4$ saturated alkyl group optionally substituted with one or more groups, which may be identical or different, chosen from —OH, —SiMe$_3$, —CO$_2$R$^6$ and —F; or
(ii) $R^1$ and $R^2$ can form, together with the nitrogen atom which bears them, a pyrrolidine heterocycle, optionally substituted with one linear ($C_1$-$C_4$) or branched ($C_3$-$C_4$) alkyl group optionally substituted with one or more OH groups; preferably, a pyrrolidine heterocycle substituted with a hydroxymethyl group;
$R^6$ representing a hydrogen atom or a linear ($C_1$-$C_4$), preferably ($C_1$-$C_2$), saturated alkyl group;
$R^3$ represents a hydrogen atom;
$R^4$ represents a hydrogen atom or —OR$^4$ represents a phosphate group; preferably, $R^4$ represents a hydrogen atom.

The preferred compounds of formula (II) are those for which:
(i) $R^1$ and $R^2$ represent a hydrogen atom, or $R^1$ represents a hydrogen atom and $R^2$ represents a linear $C_1$-$C_6$ or branched $C_3$-$C_6$ saturated alkyl group substituted with one or more groups, which may be identical or different, chosen from —OH, —SiMe$_3$, —CO$_2$R$^6$ and —F;
or
(ii) $R^1$ and $R^2$ represent a linear $C_1$-$C_6$ or branched $C_3$-$C_6$ saturated alkyl group optionally substituted with one or more groups, which may be identical or different, chosen from —OH, SiMe$_3$, —CO$_2$R$^6$ and —F;
or
(iii) $R^1$ and $R^2$ form, together with the nitrogen atom which bears them, a saturated heterocycle with 5 to 7 ring members and optionally comprising another heteroatom chosen from sulphur and oxygen; this heterocycle being optionally substituted with 1 to 3 (preferably 1) linear ($C_1$-$C_4$) or branched ($C_3$-$C_4$) alkyl group(s) optionally substituted with one or more OH groups;
$R^6$ representing a hydrogen atom or a linear ($C_1$-$C_4$) or branched ($C_3$-$C_4$) saturated alkyl group;
$R^3$ represents a hydrogen atom;
$R^4$ represents a hydrogen atom or —OR$^4$ represents a phosphate group.

Preferably, use is made of compounds of formula (II) for which:
(i) $R^1$ and $R^2$ represent a hydrogen atom, or
(ii) $R^1$ represents a hydrogen atom and $R^2$ represents a linear $C_1$-$C_4$ or branched $C_3$-$C_4$ saturated alkyl group substituted with one or more groups, which may be identical or different, chosen from —OH, —SiMe$_3$, —CO$_2$R$^6$ and —F;
or
(iii) $R^1$ and $R^2$ represent a linear $C_1$-$C_4$ or branched $C_3$-$C_4$ saturated alkyl group optionally substituted with one or more groups, which may be identical or different, chosen from —OH, SiMe$_3$, —CO$_2$R$^6$ and —F;

or
(iv) $R^1$ and $R^2$ can form, together with the nitrogen atom which bears them, a pyrrolidine heterocycle, optionally substituted with one linear ($C_1$-$C_4$) or branched ($C_3$-$C_4$) alkyl group optionally substituted with one or more OH groups; preferably, a pyrrolidine heterocycle substituted with a hydroxylmethyl group;

$R^6$ representing a hydrogen atom or a linear ($C_1$-$C_4$), preferably ($C_1$-$C_2$), saturated alkyl group;

$R^3$ represents a hydrogen atom;

$R^4$ represents a hydrogen atom or —$OR^4$ represents a phosphate group; preferably, $R^4$ represents a hydrogen atom.

The preferred compounds of formula (III) are those for which:
(i) $R^1$ represents a hydrogen atom and $R^2$ represents a linear $C_1$-$C_6$ or branched $C_3$-$C_6$ saturated alkyl group substituted with one or more groups, which may be identical or different, chosen from —OH, —SiMe$_3$, —CO$_2$R$^6$ and —F, $R^2$ not denoting a —CH$_2$—CO—O—CH$_3$ group;
or
(ii) $R^1$ and $R^2$ represent a linear $C_2$ or $C_4$-$C_6$ or branched $C_3$-$C_6$ saturated alkyl group, which is unsubstituted;
or
(iii) $R^1$ and $R^2$ represent a linear $C_1$-$C_6$ or branched $C_3$-$C_6$ saturated alkyl group substituted with one or more groups, which may be identical or different, chosen from —OH, —SiMe$_3$, —CO$_2$R$^6$ and —F;
or
(iv) $R^1$ and $R^2$ form, together with the nitrogen atom which bears them, a saturated heterocycle with 5 to 7 ring members and optionally comprising another heteroatom chosen from sulphur and oxygen, this heterocycle being optionally substituted with 1 to 3 (preferably 1) linear ($C_1$-$C_4$) or branched ($C_3$-$C_4$) alkyl group(s) optionally substituted with one or more OH groups;

$R^6$ representing a hydrogen atom or a linear ($C_1$-$C_4$) or branched ($C_3$-$C_4$) saturated alkyl group;

$R^3$ represents a hydrogen atom;

$R^4$ represents a hydrogen atom or —$OR^4$ represents a phosphate group.

Preferably, use is made of compounds of formula (III) for which:

(i) $R^1$ represents a hydrogen atom and $R^2$ represents a linear $C_1$-$C_4$ or branched $C_3$-$C_4$ saturated alkyl group substituted with one or more groups, which may be identical or different, chosen from —OH, —SiMe$_3$, —CO$_2$R$^6$ and —F, $R^2$ not denoting a —CH$_2$—CO—O—CH$_3$ group;
or
(ii) $R^1$ and $R^2$ represent a linear $C_2$ or $C_4$ or branched $C_3$-$C_6$ saturated alkyl group, which is unsubstituted;
or
(iii) $R^1$ and $R^2$ represent a linear $C_1$-$C_4$ or branched $C_3$-$C_4$ saturated alkyl group substituted with one or more groups, which may be identical or different, chosen from —OH, —SiMe$_3$, —CO$_2$R$^6$ and —F;
or
(iv) $R^1$ and $R^2$ can form, together with the nitrogen atom which bears them, a pyrrolidine heterocycle, optionally substituted with one linear ($C_1$-$C_4$) or branched ($C_3$-$C_4$) alkyl group optionally substituted with one or more OH groups; preferably, a pyrrolidine heterocycle substituted with a hydroxymethyl group;

$R^6$ representing a hydrogen atom or a linear ($C_1$-$C_4$), preferably ($C_1$-$C_2$), saturated alkyl group;

$R^3$ represents a hydrogen atom;

$R^4$ represents a hydrogen atom or —$OR^4$ represents a phosphate group; preferably $R^4$ represents a hydrogen atom.

More preferably, use is made of compounds of formula (I), (II) or (III) for which:

$R^1$ represents a hydrogen atom or a linear $C_1$-$C_4$ (preferably $C_1$-$C_2$) saturated alkyl group optionally substituted with a group chosen from —OH and —SiMe$_3$;

$R^2$ represents a linear $C_1$-$C_4$ (preferably $C_1$-$C_2$) saturated alkyl group substituted with a group chosen from —OH and —SiMe$_3$;

$R^3$ and $R^4$ represent a hydrogen atom.

Advantageously, use is made of compounds of formula (I), (II) or (III) for which:

$R^1$ represents a linear $C_1$-$C_4$ (preferably $C_1$-$C_2$) saturated alkyl group optionally substituted with an —OH group;

$R^2$ represents a linear $C_1$-$C_4$ (preferably $C_1$-$C_2$) saturated alkyl group substituted with an —OH group;

$R^3$ and $R^4$ represent a hydrogen atom.

As preferred compounds of formula (I) mention may be made of the following compounds:

| Compound | Structure | Name | CAS |
|---|---|---|---|
| 1 | 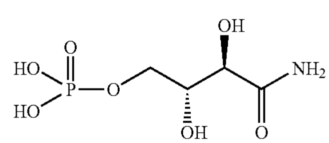 [SMILES: NC(=O)[C@H](O)[C@H](O)COP(=O)(O)O] | (2R,3R)-4-amino-2,3-dihydroxy-4-oxobutyl dihydrogen phosphate | 717921-02-3 |
| 2 | 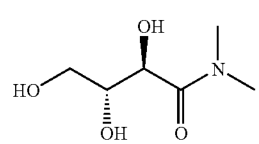 | (2R,3R)-2,3,4-trihydroxy-N,N-dimethylbutanamide | 164215-24-1 |
| 3 | 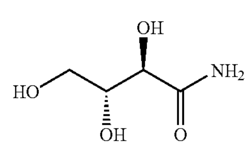 | (2R,3R)-2,3,4-trihydroxybutanamide | 73713-13-0 |

-continued

| Compound | Structure | Name | CAS |
|---|---|---|---|
| 4 | 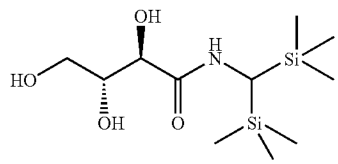 [SMILES: C[Si](C)(C)C(NC(=O)[C@H](O)[C@H](O)CO)[Si](C)(C)C] | (2R,3R)-N-[bis(trimethylsilyl)-methyl]-2,3,4-trihydroxybutanamide | — |
| 5 | 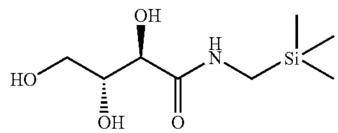 | (2R,3R)-2,3,4-trihydroxy-N-[(trimethylsilyl)-methyl]butanamide | — |
| 6 | 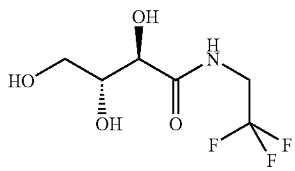 [SMILES: O=C(NCC(F)(F)F)[C@H](O)[C@H](O)CO] | (2R,3R)-2,3,4-trihydroxy-N-(2,2,2-trifluoroethyl)-butanamide | — |
| 7 | 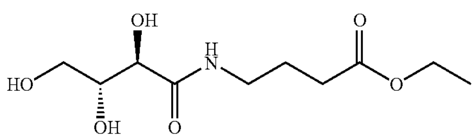 [SMILES: CCOC(=O)CCCNC(=O)[C@H](O)[C@H](O)CO] | Ethyl 4-{[(2R,3R)-2,3,4-trihyroxybutanoyl]-amino}butanoate | — |
| 8 | 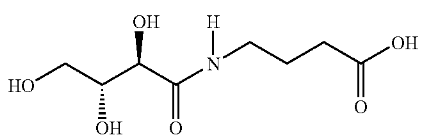 [SMILES: O=C(O)CCCNC(=O)[C@H](O)[C@H](O)CO] | 4-{[(2R,3R)-2,3,4-trihydroxybutanoyl]-amino}butanoic acid | — |
| 9 | 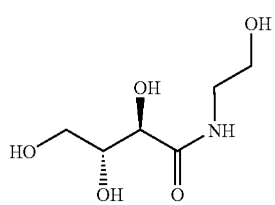 [SMILES: O=C(NCCO)[C@H](O)[C@H](O)CO] | (2R,3R)-2,3,4-trihydroxy-N-(2-hydroxyethyl)butanamide | — |
| 10 | 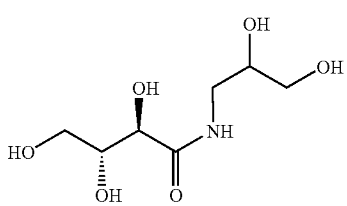 [SMILES: O=C(NCC(O)CO)[C@H](O)[C@H](O)CO] | (2R,3R)-N-(2,3-dihydroxypropyl)-2,3,4-trihydroxybutanamide | — |
| 11 | 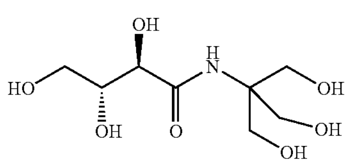 [SMILES: O=C(NC(CO)(CO)CO)[C@H](O)[C@H](O)CO] | (2R,3R)-2,3,4-trihydroxy-N-[2-hydroxy-1,1-bis(hydroxymethyl)-ethyl]butanamide | — |
| 12 | 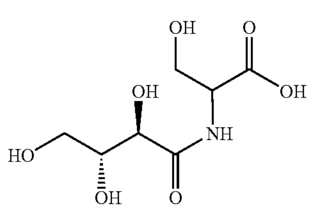 [SMILES: O=C(O)C(CO)NC(=O)[C@H](O)[C@H](O)CO] | 3-hydroxy-2-{[(2R,3R)-2,3,4-trihydroxybutanoyl]-amino}propanoic acid | — |

-continued

| Compound | Structure | Name | CAS |
|---|---|---|---|
| 13 | 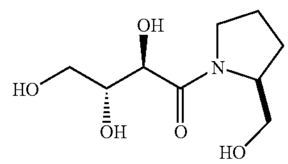 [SMILES: O=C([C@H](O)[C@H](O)CO)N1CCC[C@H]1CO] | (2R,3R)-4-[(2S)-2-(hydroxymethyl)-pyrrolidin-1-yl]-4-oxobutane-1,2,3-triol | — |
| 14 | 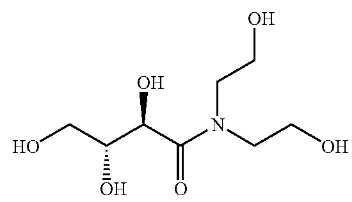 [SMILES: O=C([C@H](O)[C@H](O)CO)N(CCO)CCO] | (2R,3R)-2,3,4-trihydroxy-N,N-bis(2-hydroxyethyl)-butanamide | — |
| 15 | 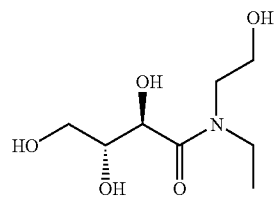 | (2R,3R)-N-ethyl-2,3,4-trihydroxy-N-(2-hydroxyethyl)-butanamide | — |
| 16 | 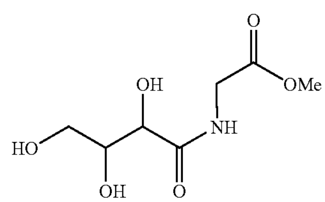 [SMILES: COC(=O)CNC(=O)C(O)C(O)CO] | methyl [(2,3,4-trihydroxybutanoyl)-amino]acetate | 60094-76-0 |
| 17 | 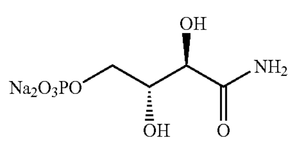 | (2R,3R)-4-amino-2,3-dihydroxy-4-oxobutyl disodium phosphate | 668990-33-8 |
| 18 | 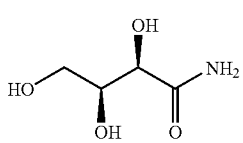 | (2R,3S)-2,3,4-trihydroxybutanamide | 74421-65-1 |
| 19 | 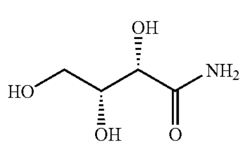 | (2S,3R)-2,3,4-trihydroxybutanamide | 74464-43-0 |
| 20 | 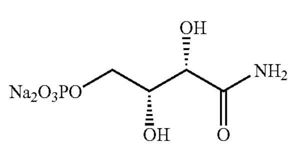 | (2R,3S)-4-amino-2,3-dihydroxy-4-oxobutyl-disodium phosphate | 798554-52-6 |

| Compound | Structure | Name | CAS |
| --- | --- | --- | --- |
| 21 | H₂O₃PO—CH₂—CH(OH)—CH(OH)—C(O)—NH₂ (with (2R,3S) stereochemistry shown) | (2R,3S)-4-amino-2,3-dihydroxy-4-oxobutyl-dihydrogen phosphate | 807318-55-4 |
| 22 | HO—CH₂—CH(OH)—CH(OH)—C(O)—NH₂ (with (2S,3S) stereochemistry shown) | (2S,3S)-2,3,4-trihydroxybutanamide | 74421-64-0 |

The preferred compounds of formula (II) are chosen from compounds 2 to 15 mentioned above.

The preferred compounds of formula (III) are chosen from compounds 4 to 15 mentioned above.

Compounds 3, 5, 9, 14 and 15 are particularly preferred, and more particularly compounds 14 and 15.

The compounds of formula (I) for which $R^3=R^4=H$ (compounds 1a) can be obtained by reacting the methyl ester of threonic acid or erythronic acid (A) (these two compounds differ from one another according to the configuration of the asymmetrical carbons) with an amine $HN(R^1)(R^2)$ in particular in ethanol or acetonitrile, at a temperature of approximately 60° C.

The compounds of formula (I) for which $—OR^3$ and $—OR^4$ denote a phosphate group (compounds Ib) can be prepared by deprotonation of the methyl ester of threonic acid or erythronic acid (A) in the presence of a base such as sodium hydride or triethylamine or pyridine, and then nucleophilic substitution by reaction with a phosphating agent such as a dialkyl phosphate chloride (for example, dimethyl chlorophosphate or diphenyl chlorophosphate) or a trialkyl phosphite (for example, trimethyl phosphite or tribenzyl phosphite) or alternatively a pyrophosphate (for example, tetrabenzyl pyrophosphate). The phosphate esters thus obtained are subsequently converted to phosphate or their salt, either by hydrolysis in an acidic or basic medium, or by treatment using a bromide ion (for example, lithium bromide or trimethylsilyl bromide), or by hydrogenolysis using molecular hydrogen in the presence of a catalyst (for example, palladium-based or platinum-based).

These reactions are known from the following articles:

Dardonville C et al., "Selective inhibition of *Trypanosoma brucei* 6-phosphogluconate dehydrogenase by high-energy intermediate and transition-state analogues"; Journal of Medicinal Chemistry, 2004, 47, 13, 3427-3437;

Burgos, Emmanuel et al.; "Synthesis and evaluation of new 4-phospho-D-erythronic acid derivatives as competitive inhibitors of spinach ribose-5-phosphate isomerase"; Tetrahedron Letters (2004), 45(4), 753-756;

Phaosiri, Chanokporn et al.; "Substrate analogs for the investigation of deoxyxylulose 5-phosphate reductoisomerase inhibition: synthesis and evaluation"; J. Bioorganic & Medicinal Chemistry Letters (2004), 14(21), 5309-5312;

Walker, Joel R. et al.; "Synthesis and Evaluation of 1-Deoxy-D-xylulose 5-Phosphate Analogs as Chelation-Based Inhibitors of Methylerythritol Phosphate Synthase"; Journal of Organic Chemistry (2005), 70(24), 9955-9959.

The compounds of formula (I) for which the two groups $R^3$ taken together form an isopropylidene group and $R^4=H$ (compounds Ic) can be prepared by reacting the methyl ester of threonic acid or erythronic acid (A) with acetone so as to form the isopropylidene derivative (B) which, by reacting with an amine $HN(R^1)(R^2)$, in particular in ethanol or acetonitrile, at a temperature of approximately 60° C., gives the compound (Ic).

The compounds of formula (I) for which the two groups $R^3$ taken together form an isopropylidene group and $—OR^4$ denotes a phosphate group (compounds Id) can be prepared by deprotonation of the isopropylidene derivative (B) in the presence of a base such as sodium hydride or triethylamine or pyridine, and then nucleophilic substitution by reaction with a phosphating agent such as an alkyl phosphate chloride (for example, dimethyl chlorophosphate or diphenyl chlorophosphate) or a trialkylphosphite (for example, tribenzyl phosphite) or alternatively a pyrophosphate (for example, tetrabenzyl pyrophosphate). The phosphate esters thus obtained are subsequently converted to phosphate or their salt as described above. These compounds subsequently react with an amine $HN(R^1)(R^2)$, in particular in ethanol or acetonitrile, at a temperature of approximately 60° C., and give the compound (Id).

The compounds of formula (I) for which $R^3=H$ and $—OR^4$ denotes a phosphate group (compounds Ie) can be prepared by deprotection of the compound (Id), in particular with dilute hydrochloric acid or an acidic resin (for example, the styrene-divinylbenzene resin comprising a sulphonic acid functional group, sold under the name Dowex® 50WX 8 hydrogen form 100-200 mesh from Dow Chemical, and in particular sold by the company Sigma-Aldrich) in a solvent such as water, ethanol or tetrahydrofuran, in particular at a temperature ranging from 20° C. to 60° C.

Scheme I

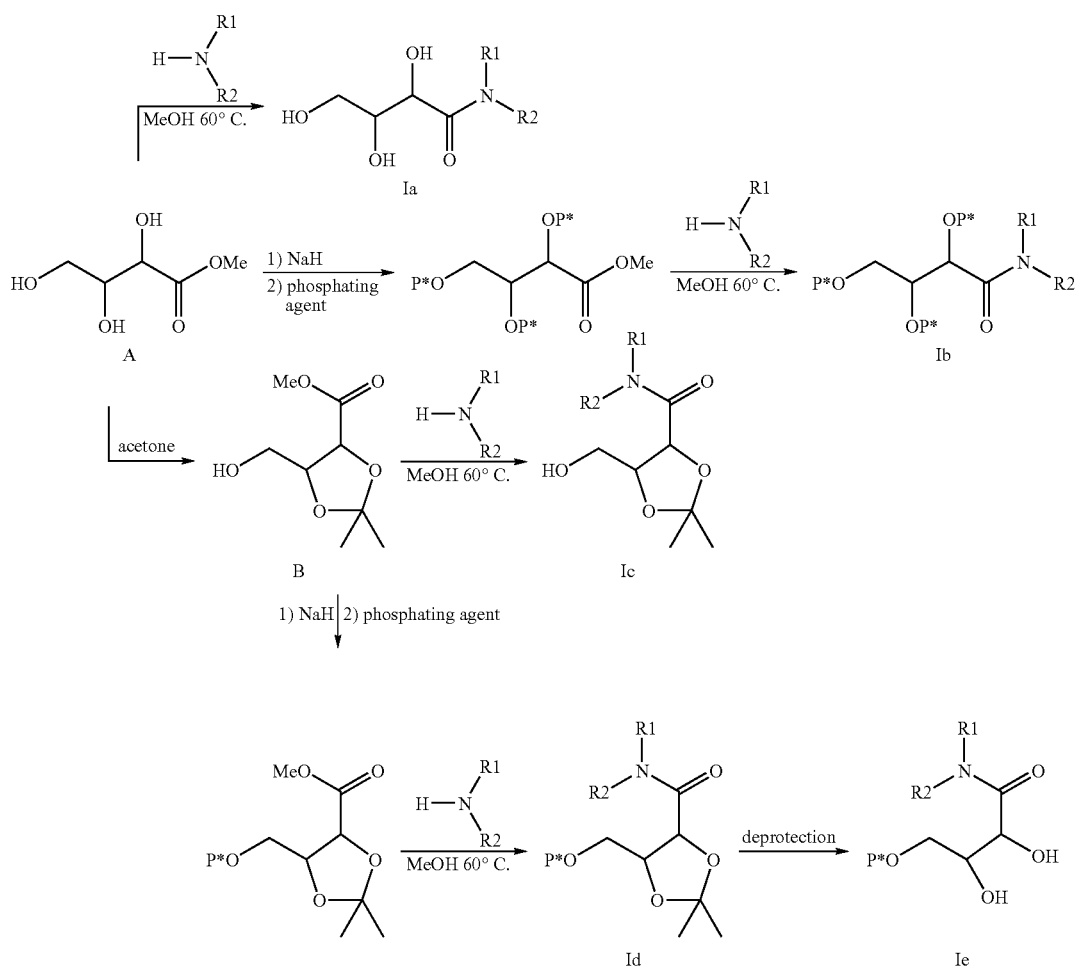

P* denotes a group P=O(OR)₂
R = H, or salt

According to another method of synthesis (Scheme II), the compounds of formula (I) for which R³=R⁴=H (compounds Ia) can be prepared by mixing, in particular at a temperature of between 0 and 100° C., D-erythronolactone (C) and an amine R¹—NH—R², without solvent or in a polar, protic or aprotic solvent, for instance water, ethanol, methanol or acetonitrile.

The compounds of formula (I) for which —OR³ denotes a phosphate group and R⁴=H (compounds If) can be prepared by deprotonation of the D-erythronolactone (C) in the presence of a base such as sodium hydride or triethylamine or pyridine, and then nucleophilic substitution by reaction with a phosphating agent such as a dialkyl phosphate chloride (for example, dimethyl chlorophosphate or diphenyl chlorophosphate) or a trialkyl phosphite (for example, dimethyl phosphite or tribenzyl phosphite) or alternatively a pyrophosphate (for example, tetrabenzyl pyrophosphate). The phosphate esters thus obtained are subsequently converted to phosphate or their salt as described above, so as to form the compound (D), which subsequently reacts with an amine HN(R¹)(R²) in particular in an apolar solvent such as dichloromethane, at a temperature of approximately 60° C. The step for conversion of the phosphate esters to phosphates and their salts can be carried out after the formation of the amide.

The compounds of formula (I) for which the two groups R³ taken together form an isopropylidene group and —OR⁴=H (compounds Ic) can be prepared by reacting the isopropylidene of D-erythronolactone (E) (compound known under CAS No. 25581-41-3) with an amine HN(R¹)(R²) in particular in a polar, protic or aprotic solvent, or an apolar solvent (for example, dichloromethane), at a temperature of between 30 and 60° C.

The compounds of formula (I) for which R³=H and —OR⁴ denotes a phosphate group (compounds Ie) can be prepared from the compound (Ic) by phosphation of the free hydroxyl by reaction with a phosphating agent as described above, and then by deprotection, in particular with dilute hydrochloric acid or an acidic resin (for example, the styrene-divinylbenzene resin comprising a sulphonic acid functional group, sold under the name Dowex® 50WX 8 hydrogen form 100-200 mesh from Dow Chemical, and in particular sold by the company Sigma-Aldrich), in a solvent such as water, ethanol or tetrahydrofuran, in particular at a temperature ranging from 20° C. to 60° C.

The methods of synthesis of Scheme II make it possible to prepare compounds with an R, R stereochemistry with respect to the 2 asymmetrical carbons.

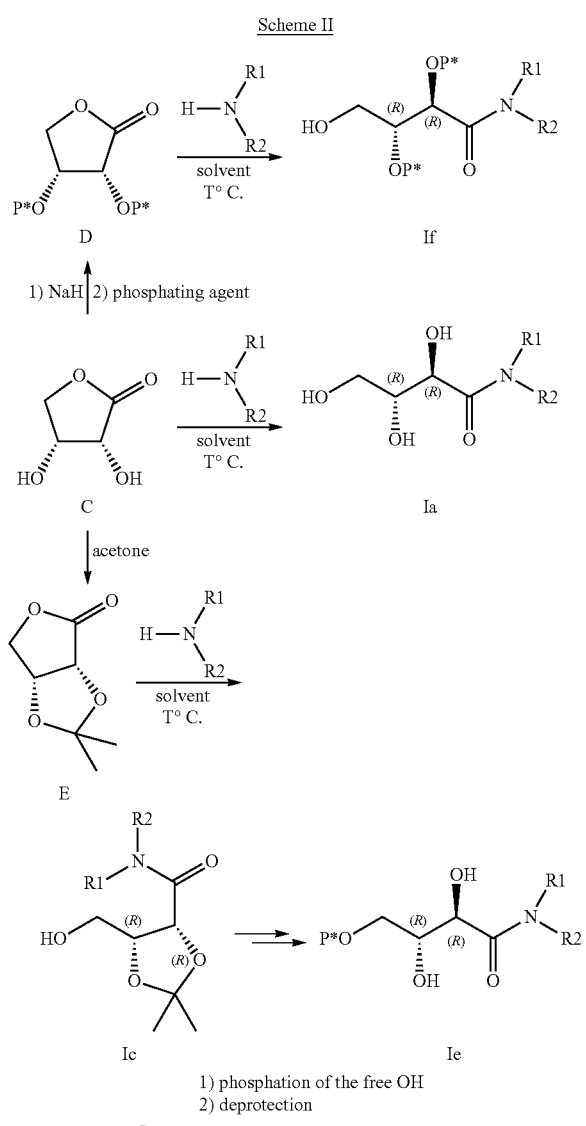

Scheme II

P* denotes a group P=O(OR)$_2$
R = H, or salt

It should be noted that, when the $R^1$ and/or $R^2$ groups denote a saturated $C_1$-$C_6$ or unsaturated $C_2$-$C_6$ linear alkyl group or saturated or unsaturated $C_3$-$C_6$ branched alkyl group, substituted with one or more $CO_2R^6$ groups, which may be identical or different, the latter can be obtained by means of simple chemical conversions known to those skilled in the art, such as an esterification (of a —COOH group), a saponification or a hydrolysis (of a corresponding ester group).

The present invention also relates to a composition comprising, in a physiologically acceptable medium, a compound of formula (II) as described above. The composition is in particular a cosmetic or dermatological composition.

These cosmetic compositions in which the compounds (II) (or the compounds of formula (I) for the use described above) may be employed can be used for non-therapeutic skincare and/or making up the skin. They can in particular be used for moisturizing the skin.

They can show their effectiveness as a non-therapeutic skin maintenance treatment, i.e. by way of prevention. They can also be used by way of non-therapeutic treatment of the skin after a manifestation of skin moisturization problems.

In this second case, this manifestation of skin moisturization problems is preferably independent of an irritation caused by the skin coming into contact with a bleaching, in particular chlorinated, agent, for example a hypochlorite-based agent.

Finally, the cosmetic compositions of the invention are preferably formulated under non-alkaline conditions, even more preferably at a pH close to that of the skin, for example at a pH of between 5 and 6.

The compounds of formula (I) or (II) may be present in the cosmetic compositions at contents ranging from 0.01% to 20%, preferably from 0.01% to 15%, and even more preferably from 0.1% to 10% by weight relative to the total weight of the cosmetic composition.

The compositions used according to the invention contain a physiologically acceptable medium, i.e. a medium compatible with cutaneous tissues such as the skin and the scalp. This physiologically acceptable medium may consist more particularly of water and, optionally, of a physiologically acceptable organic solvent chosen, for example, from lower alcohols containing from 1 to 8 carbon atoms, and in particular from 1 to 6 carbon atoms, such as ethanol, isopropanol, propanol or butanol; polyethylene glycols having from 6 to 80 ethylene oxide units and polyols such as propylene glycol, isoprene glycol, butylene glycol, glycerol and sorbitol.

The compositions according to the invention can be in any of the pharmaceutical forms conventionally used for topical application, and in particular in the form of aqueous or aqueous-alcoholic solutions, oil-in-water (O/W) or water-in-oil (W/O) or multiple (triple: W/O/W or O/W/O) emulsions, aqueous gels, or dispersions of a fatty phase in an aqueous phase by means of spherules, it being possible for these spherules to be polymeric nanoparticles such as nanospheres and nanocapsules, or lipid vesicles of ionic and/or non-ionic type (liposomes, niosomes, oleosomes). These compositions are prepared according to the usual methods.

In addition, the compositions used according to the invention may be more or less fluid and may have the appearance of a white or coloured cream, an ointment, a milk, a lotion, a serum, a paste or a foam. They may be optionally applied to the skin in the form of an aerosol. They may also be in solid form, and for example in the form of a stick.

When the composition used according to the invention comprises an oily phase, the latter preferably contains at least one oil. It can also contain other fatty substances.

As oils that can be used in the composition of the invention, mention may, for example, be made of:

hydrocarbon-based oils of animal origin, such as perhydrosqualene;

hydrocarbon-based oils of plant origin, such as liquid triglycerides of fatty acids containing from 4 to 10 carbon atoms, such as heptanoic or octanoic acid triglycerides, or alternatively, for example, sunflower oil, maize oil, soybean oil, marrow oil, grapeseed oil, sesame oil, hazelnut oil, apricot oil, macadamia oil, arara oil, castor oil, avocado oil, caprylic/capric acid triglycerides, such as those sold by the company Stearineries Dubois or those sold under the names "Miglyol 810", "812" and "818" by the company Dynamit Nobel, jojoba oil and shea butter;

synthetic esters and ethers, in particular of fatty acids, for instance oils of formulae R1COOR2 and R1OR2 in which R1 represents a fatty acid residue containing from 8 to 29 carbon atoms, and R2 represents a branched or unbranched hydrocarbon-based chain comprising from 3 to 30 carbon atoms, for instance purcellin oil, isononyl isononanoate, isopropyl myristate, 2-ethylhexyl palmitate, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate, triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, and hydrogenated polyisobutene such as parleam oil;

fatty alcohols containing from 8 to 26 carbon atoms, such as cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

fluoro oils that are partially hydrocarbon-based and/or silicone-based, such as those described in document JP-A-2-295912;

silicone oils, such as volatile or non-volatile polymethylsiloxanes (PDMS) with a linear or cyclic silicone chain, which are liquid or pasty at ambient temperature, in particular cyclopolydimethylsiloxanes (cyclomethicones), such as cyclohexasiloxane; polydimethylsiloxanes comprising alkyl, alkoxy or phenyl groups, which are pendent or at the end of a silicone chain, these groups containing from 2 to 24 carbon atoms; phenylsilicones, such as phenyl trimethicones, phenyl dimethicones, phenyltrimethylsiloxydiphenylsiloxanes, diphenyl dimethicones, diphenylmethyl-diphenyltrisiloxanes or 2-phenylethyl trimethylsiloxy silicates, and polymethylphenylsiloxanes;

mixtures thereof.

In the list of oils mentioned above, the term "hydrocarbon-based oil" is intended to mean any oil comprising predominantly carbon and hydrogen atoms, and possibly ester, ether, fluoro, carboxylic acid and/or alcohol groups.

The other fatty substances that may be present in the oily phase are, for example, fatty acids containing from 8 to 30 carbon atoms, such as stearic acid, lauric acid, palmitic acid and oleic acid; waxes such as lanolin, beeswax, carnauba wax or candelilla wax, paraffin wax, lignite wax or microcrystalline wax, ceresin or ozokerite, synthetic waxes such as polyethylene waxes and Fischer-Tropsch waxes; silicone resins such as trifluoromethyl-C1-4-alkyl dimethicone and trifluoropropyl dimethicone; and silicone elastomers, such as the products sold under the names "KSG" by the company Shin-Etsu, under the names "Trefil", "BY29" or "EPSX" by the company Dow Corning or under the names "Gransil" by the company Grant Industries.

These fatty substances can be chosen in a varied manner by those skilled in the art, so as to prepare a composition having the desired properties, for example in terms of consistency and texture.

According to a specific embodiment of the invention, the composition according to the invention is a water-in-oil (W/O) or oil-in-water (O/W) emulsion. The proportion of the oily phase of the emulsion can range from 5% to 80% by weight, and preferably from 5% to 50% by weight relative to the total weight of the composition.

The emulsions generally contain at least one emulsifier chosen from amphoteric, anionic, cationic or non-ionic emulsifiers, used alone or as a mixture, and optionally a co-emulsifier. The emulsifiers are chosen in an appropriate manner according to the emulsion to be obtained (W/O or O/W). The emulsifier and the co-emulsifier are generally present in the composition in a proportion ranging from 0.3% to 30% by weight, and preferably from 0.5% to 20% by weight relative to the total weight of the composition.

For the W/O emulsions, examples of emulsifiers that may be mentioned include dimethicone copolyols such as the mixture of cyclomethicone and of dimethicone copolyol sold under the name "DC 5225 C" by the company Dow Corning, and alkyl dimethicone copolyols such as the laurylmethicone copolyol sold under the name "Dow Corning 5200 Formulation Aid" by the company Dow Corning and the cetyl dimethicone copolyol sold under the name "Abil EM 90®" by the company Goldschmidt. Surfactants for W/O emulsions that may also be used include a crosslinked elastomeric solid organopolysiloxane comprising at least one oxyalkylene group, such as those obtained according to the procedure of examples 3, 4 and 8 of document U.S. Pat. No. 5,412,004, and of the examples of document U.S. Pat. No. 5,811,487, in particular the product in example 3 (synthesis example) of patent U.S. Pat. No. 5,412,004, and such as those sold under the reference KSG 21 by the company Shin Etsu.

For the O/W emulsions, examples of emulsifiers that may be mentioned include non-ionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; and mixtures thereof such as the mixture of glyceryl stearate and of PEG-40 stearate.

In a known manner, the cosmetic or dermatological composition of the invention may also contain adjuvants that are common in the cosmetics or dermatology field, such as oils, waxes, thickeners, film-forming polymers, preserving agents, fragrances, fillers, UV-screening agents, bactericides, odour absorbers, dyestuffs, cosmetic active agents, plant extracts and antioxidants. The amounts of these various adjuvants are those conventionally used in the field under consideration, and for example from 0.01% to 20% of the total weight of the composition. Depending on their nature, these adjuvants may be introduced into the fatty phase and/or into the aqueous phase.

The compounds of formula (II) can be combined with one another, or with other additional skin moisturizers other than the compounds of formula (II) described above and/or with at least one other cosmetic active agent.

Additional cosmetic active agents that may in particular be mentioned include active agents that act on the barrier function of the skin, active agents that promote skin moisturization and desquamating agents.

The term "desquamating agent" is intended to mean any compound capable of acting:

either directly on desquamation by promoting exfoliation, such as β-hydroxy acids, in particular salicylic acid and derivatives thereof (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of *Saphora japonica*; resveratrol;

or on the enzymes involved in desquamation or corneodesmosome degradation, such as glycosidases, stratum corneum chymotryptic enzyme (SCCE) or other proteases (trypsin, trypsin-like). Mention may be made of mineral salt chelating agents: EDTA; N-acyl-N,N',N'-ethylenediaminetriacetic acid; aminosulphonic compounds, and in particular N-(2-hydroxyethyl)piperazine-N'-2-ethanesulphonic acid (HEPES); derivatives of 2-oxothiazolidine-4-carboxylic acid (procystein); derivatives of alpha-amino acids of glycine type (as described in EP-0 852 949, and also sodium methyl glycine diacetate sold by BASF under the trade name "TRILON M"); honey; sugar derivatives such as O-octanoyl-6-D-maltose and N-acetylglucosamine.

Among the active agents that act on the barrier function of the skin, or that promote skin moisturization, mention may be made of:
- either compounds that act on the barrier function for the purpose of maintaining the moisturization of the stratum corneum, or occlusive compounds, in particular ceramides, sphingoid-based compounds, lecithins, glycosphingolipids, phospholipids, cholesterol and derivatives thereof, phytosterols (stigmasterol, β-sitosterol, campesterol), essential fatty acids, 1,2-diacylglycerol, 4-chromanone, pentacyclic triterpenes such as ursolic acid, petroleum jelly and lanolin;
- or compounds that directly increase the water content of the stratum corneum, such as threalose and derivatives thereof, hyaluronic acid and derivatives thereof, glycerol, pentanediol, sodium pidolate, serine, xylitol, sodium lactate, polyglyceryl acrylate, ectoin and derivatives thereof, chitosan, oligosaccharides and polysaccharides, cyclic carbonates, N-lauroylpyrrolidonecarboxylic acid, and N-α-benzoyl-L-arginine;
- or compounds that activate the sebaceous glands, such as steroidal derivatives (including DHEA) and vitamin D and derivatives thereof.

The composition may be in the form of a non-therapeutic care or make-up product, and also in the form of a lip balm.

Finally, a subject of the invention is a cosmetic treatment process for non-therapeutic skincare and/or for making up the skin, characterized in that it comprises the application to the skin of at least one cosmetic or dermatological composition according to the present invention comprising at least one compound of formula (II) as defined above or a mixture thereof in all proportions.

Among the applications of make-up type that the cosmetic treatment process makes it possible to envisage, mention may in particular be made of foundations, makeup rouges, eyeshadows, concealer products and body makeup.

Finally, the invention relates to the use of a compound of formula (II) as defined above, for the preparation of a dermatological composition for moisturizing the skin, and more particularly for use in the treatment of dryness of the skin or in the treatment of dry skin.

The examples below illustrate the invention without, however, limiting the scope thereof.

EXAMPLE 1

Preparation of (2R,3R)-N-[bis(trimethylsilyl)methyl]-2,3,4-trihydroxybutanamide (compound 4)

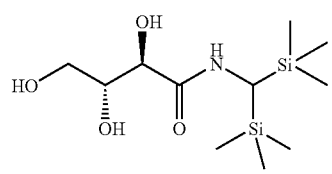 [SMILES: C[Si](C)(C)C(NC(=O)[C@H](O)[C@H](O)CO)[Si](C)(C)C]

This compound is obtained by reacting 354 mg (3 mmol) of D-erythronolactone with 580 mg (1.1 equivalents; 3.3 mmol) of amine in 6 ml of acetonitrile.

The reaction medium is agitated and the progression of the reaction is followed by thin layer chromatography on silica with visualization using a potassium permanganate solution.

Once the reaction is complete, the reaction medium is diluted in water or ethanol and Dowex 50WX8 resin (Aldrich CAS 11119-67-8) is added thereto in order to trap the excess amine. The resin is washed with water and with ethanol and the filtrate is evaporated under vacuum in order to recover the amide obtained in the form of a colourless oil.

NMR ($^1$H, $^{13}$C, DMSO d6): The spectra obtained are in accordance with the proposed structure.

Elemental analysis:

| Theoretical | Theoretical 0.5 mol of water | Measured |
|---|---|---|
| % C % H % N | % C % H % N | % C % H % N |
| 45/9.3/4.8 | 43.7/9.3/4.6 | 43.7/9.3/4.6 |

EXAMPLE 2

Preparation of (2R,3R)-2,3,4-trihydroxy-N-[(trimethyl-silyl)methyl]butanamide (compound 5)

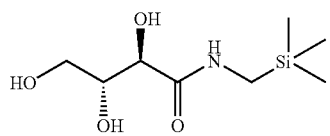

This compound is obtained according to the procedure described in example 1 using trimethylsilylmethylamine.

The amide obtained is in the form of a white solid.

NMR ($^1$H, $^{13}$C, DMSO d6): The spectra obtained are in accordance with the proposed structure.

Elemental analysis:

| Theoretical | Measured |
|---|---|
| % C % H % N | % C % H % N |
| 43.4/8.7/6.3 | 43.7/8.8/6.3 |

EXAMPLE 3

Preparation of (2R,3R)-2,3,4-trihydroxy-N-(2,2,2-trifluoroethyl)butanamide (compound 6)

This compound is obtained according to the procedure described in example 1 using trifluoroethylamine.

The amide obtained is in the form of a colourless oil.

EXAMPLE 4

Preparation of ethyl 4-{[(2R,3R)-2,3,4-trihydroxy-butanoyl]amino}butanoate (compound 7)

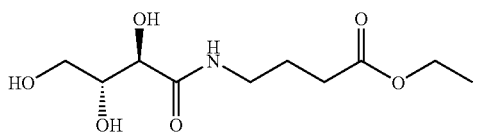 [SMILES: CCOC(=O)CCCNC(=O)[C@H](O)[C@H](O)CO]

This compound is obtained according to the procedure described in example 1 using ethyl gamma-aminobutyrate.
The amide obtained is in the form of a light yellow oil.
NMR ($^1$H, $^{13}$C, DMSO d6): The spectra obtained are in accordance with the proposed structure.
Elemental analysis: presence of water and of ethanol

| Theoretical | Theoretical 1 mol of water and 1 mol of ethanol | Measured |
| --- | --- | --- |
| % C % H % N % O<br>48.2/7.7/5.6/38.5 | % C % H % N % O<br>46/8.6/4.5/40.9 | % C % H % N % O<br>46/8/4.9/41.5 |

EXAMPLE 5

Preparation of 4-{[(2R,3R)-2,3,4-trihydroxy-butanoyl]amino}butanoic acid (compound 8)

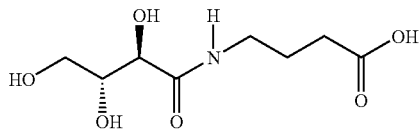 [SMILES: O=C(O)CCCNC(=O)[C@H](O)[C@H](O)CO]

This compound is obtained by saponification of compound 7 (example 4) using sodium hydroxide, followed by acidification of the carboxylate formed, with hydrochloric acid.
The amide obtained is in the form of a colourless oil.

EXAMPLE 6

Preparation of (2R,3R)-2,3,4-trihydroxy-N-(2-hydroxyethyl)butanamide (compound 9)

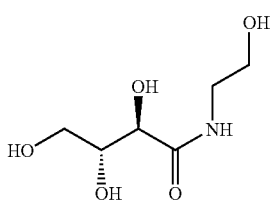

This compound is obtained according to the procedure described in example 1 using ethanolamine.
The amide obtained is in the form of a colourless oil.
NMR ($^1$H, $^{13}$C, DMSO, d6): The spectra obtained are in accordance with the proposed structure.

Elemental analysis:

| Theoretical | Theoretical 0.75 mol of water | Measured |
| --- | --- | --- |
| % C % H % N % O<br>40.2/7.3/7.8/44.6 | % C % H % N % O<br>37.4/7.5/7.2/47.7 | % C % H % N % O<br>37.5/7.5/7.3/47.3 |

EXAMPLE 7

Preparation of (2R,3R)-N-(2,3-dihydroxypropyl)-2,3,4-trihydroxybutanamide (compound 10)

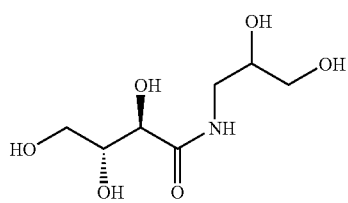

This compound is obtained according to the procedure described in example 1 using 3-amino-1,2-propanediol and using an acetonitrile/ethanol mixture.
The amide obtained is in the form of a colourless oil.
NMR ($^1$H, $^{13}$C, DMSO d6): The spectra obtained are in accordance with the proposed structure. Mixture of two diastereoisomers in 50/50 proportion.

EXAMPLE 8

Preparation of (2R,3R)-2,3,4-trihydroxy-N-[2-hydroxy-1,1-bis(hydroxymethyl)ethyl]butanamide (compound 11)

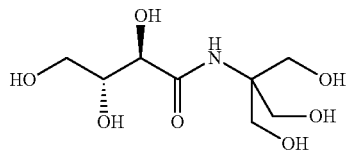 [SMILES: O=C(NC(CO)(CO)CO)[C@H](O)[C@H](O)CO]

This compound is obtained according to the procedure described in example 1 using trishydroxymethyl-methanamine and an ethanol/water mixture.
The amide obtained is in the form of a colourless oil.
NMR ($^1$H, $^{13}$C, DMSO d6): The spectra obtained are in accordance with the proposed structure.
Elemental analysis:

| Theoretical | Theoretical 2 mol of water | Measured |
| --- | --- | --- |
| % C % H % N % O<br>40.2/7.2/5.9/46.8 | % C % H % N % O<br>34.9/7.7/5.1/52.3 | % C % H % N % O<br>35.3/7.5/5/49.7 |

EXAMPLE 9

Preparation of 3-hydroxy-2-{[(2R,3R)-2,3,4-trihydroxy-butanoyl]amino}propanoic acid (compound 12)

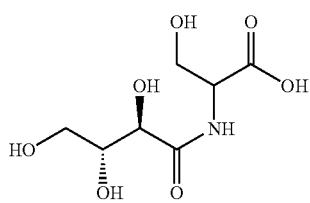 [SMILES: O=C(O)C(CO)NC(=O)[C@H](O)[C@H](O)CO]

This compound is obtained by the action of DL-serine methyl ester on D-erythronolactone, followed by saponification using sodium hydroxide and acidification of the carboxylate formed, with hydrochloric acid.

The amide obtained is in the form of a white solid.

EXAMPLE 10

Preparation of (2R,3R)-4-[(2S)-2-(hydroxymethyl)pyrrolidin-1-yl]-4-oxobutane-1,2,3-triol (compound 13)

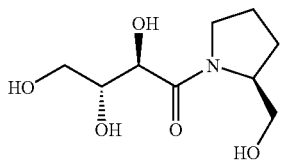 [SMILES: O=C([C@H](O)[C@H](O)CO)N1CCC[C@H]1CO]

This compound is obtained according to the procedure described in example 1 using D-prolinol.

The amide obtained is in the form of a colourless oil.

NMR ($^1$H, $^{13}$C, DMSO d6): The spectra obtained are in accordance with the proposed structure.

Elemental analysis:

| Theoretical | Theoretical 1.15 mol of water | Measured |
|---|---|---|
| % C / % H / % N / % O | % C / % H / % N / % O | % C / % H / % N / % O |
| 49.3/7.8/6.4/36.5 | 45/8/5.8/41 | 44.7/8/5.8/39 |

EXAMPLE 11

Preparation of (2R,3R)-2,3,4-trihydroxy-N,N-bis(2-hydroxyethyl)butanamide (compound 14)

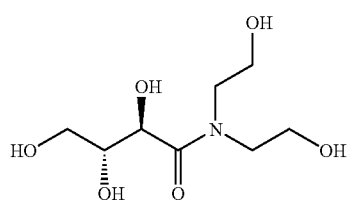 [SMILES: O=C([C@H](O)[C@H](O)CO)N(CCO)CCO]

This compound is obtained according to the procedure described in example 1 using diethanolamine.

The amide obtained is in the form of a colourless oil.

NMR ($^1$H, $^{13}$C, DMSO d6): The spectra obtained are in accordance with the proposed structure.

Elemental analysis:

| Theoretical | Theoretical 1 mol of water | Measured |
|---|---|---|
| % C / % H / % N / % O | % C / % H / % N / % O | % C / % H / % N / % O |
| 43/7.7/6.3/43 | 39.8/7.9/5.8/46.4 | 38.9/7.9/5.8/46.8 |

EXAMPLE 12

Preparation of (2R,3R)-N-ethyl-2,3,4-trihydroxy-N-(2-hydroxyethyl)butanamide (compound 15)

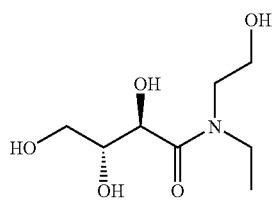

This compound is obtained according to the procedure described in example 1 using N-ethylethanolamine in ethanol.

The amide obtained is in the form of a colourless oil.

NMR ($^1$H, $^{13}$C, DMSO d6): The spectra obtained are in accordance with the proposed structure.

EXAMPLE 13

Cosmetic Formulations

EXAMPLE 13.1

Skincare Cream

A skincare cream composition comprising the following ingredients is prepared:

| PHASE A | |
|---|---|
| Glyceryl stearate (and) PEG-100 stearate: | 2.00 g |
| Dimyristyl tartrate (and) cetearyl alcohol (and) C12-15 pareth-7 (and) PPG-25 laureth-25: | 1.50 g |
| Cyclohexasiloxane | 5.00 g |
| Stearyl alcohol | 1.00 g |
| PHASE B | |
| Water: | QS 100 g |
| Pentasodium ethylenediaminetetramethylene phosphate: | 0.05 g |
| Ammonium polyacryldimethyltauramide: | 0.40 g |
| Xanthan gum: | 0.20 g |
| PHASE C | |
| (2R, 3R)-2,3,4-trihydroxybutanamide, compound 3 | 5.00 g |
| Glycerol | 1.50 g |
| Adenosine | 0.10 g |
| Water | 3.00 g |

Procedure

Phase B is heated to approximately 75° C. and the ammonium polyacryldimethyltauramide is incorporated therein; the mixture is stirred until a homogeneous gel is obtained.

Phase A is heated to approximately 75° C.

The emulsion is prepared by incorporating phase A into phase B.

At 40-45° C., phase C is incorporated and the stirring is maintained until complete cooling.

Skincare creams are also prepared according to this formula with the compounds B, D, E, H and K.

EXAMPLE 13.2

Skincare Cream

A skincare composition comprising the following ingredients is prepared:

| | |
|---|---|
| (2R, 3R)-2,3,4-trihydroxy-N-[2-hydroxy-1,1-bis (hydroxymethyl) ethyl]butanamide, compound 11 | 3.0% |
| Glyceryl monostearate | 0.8% |
| Cetyl alcohol | 2.0% |
| Stearyl alcohol | 5.0% |
| Polyoxyethylene stearate (20 EO) | 3.0% |
| Crosslinked acrylic acid (CARBOPOL 941) | 0.3% |
| Caprylic/capric triglycerides | 12.0% |
| Preserving agents | qs |
| Water | qs 100.0% |

Skincare creams are also prepared according to this formulation with the compounds B, C, F, I and J.

The exemplified cosmetic formulations applied to the skin show a good skin-moisturizing effect.

EXAMPLE 14

Evaluation of the Moisturizing Potential

A test was performed to evaluate the moisturizing potential of the compounds of the invention which are formulated in a 3% aqueous solution.

Dermometer, mechanical measurement of the plasticizing effect (described by J de Rigal, J-L. Leveque, *International Journal of Cosmetic Science*, 1982, 247-260).

The tests carried out were performed under the standard conditions on stratum corneum in a chamber at controlled temperature and humidity (T=30° C. and RH=75%). The elastic modulus measurements are performed on each control test specimen and then 2 hours and 20 hours after application of the treatment. The relative variation in the modulus makes it possible to assess the plasticizing effect of the active agent on the Stratum Corneum.

TABLE 1

Dermometer measurements: Relative variation in the elastic modulus of *Stratum Corneum* at 30° C. and 75% relative humidity, 2 h and 20 h after application of the active agent

| | (Mean ± standard deviation) | |
|---|---|---|
| Product | 2 H | 20 H |
| Products tested at 3% in water | | |
| Compound 3 | −32 +/− 18% | −34 +/− 15% |
| Compound 5 | −34 +/− 15 | −31 +/− 18 |
| Compound 9 | −26 +/− 14% | −27 +/− 16% |
| Compound 14 | −23 +/− 18 | −49 +/− 14 |
| Compound 15 | −28 +/− 10 | −48 +/− 12 |
| Control products in water | | |
| Pure water | −5 ± 11% | −6 ± 12% |
| Urea | −72 ± 9% | −83 ± 7% |
| Glycerol | −41 ± 12% | −51 ± 15% |

The mean and the standard deviation were calculated on 10 stratum corneum samples.

Compounds 3, 5, 9, 14 and 15 have a significant plasticizing effect on the stratum corneum, compounds 14 and 15 being the most effective.

It emerges from this test that the compounds for use according to the invention have different "moisturizing" profiles in plasticizing the Stratum Corneum.

The invention claimed is:
1. A method for cosmetic moisturization of the skin comprising applying to the skin a compound of formula (I):

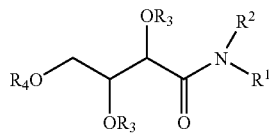

wherein
(i) $R^1$ and $R^2$ represent, independently of one another, a hydrogen atom, or a saturated $C_1$-$C_6$ or unsaturated $C_2$-$C_6$ linear alkyl group or saturated or unsaturated $C_3$-$C_6$ branched alkyl group, optionally substituted with one or more groups, which may be identical or different, selected from the group consisting of —$OR^5$, —$SiMe_3$, —$CO_2R^6$ and —F; or
(ii) $R^1$ and $R^2$ can form, together with the nitrogen atom which bears them, a saturated heterocycle with 5 to 7 ring members, and optionally comprising another heteroatom chosen from sulphur and oxygen, this heterocycle being optionally substituted with 1 to 3 linear $C_1$-$C_4$ or branched $C_3$-$C_4$ alkyl group(s) optionally substituted with one or more OH groups;
$R^5$ representing a hydrogen atom, or a linear $C_1$-$C_3$ or branched $C_3$ saturated, or $C_2$-$C_3$ unsaturated alkyl group;
$R^6$ representing a hydrogen atom or a linear $C_1$-$C_4$ or branched $C_3$-$C_4$ saturated alkyl group;
$R^3$ represents a hydrogen atom or a linear $C_1$-$C_6$ saturated alkyl group, or —$OR^3$ represents a phosphate group; it being possible for the two groups $R^3$ to form, together, an isopropylidene group;
$R^4$ represents a hydrogen atom or —$OR^4$ represents a phosphate group;
and the salts, isomers and solvates thereof.
2. The method according to claim 1, wherein in the compound of formula (I):
(i) $R^1$ and $R^2$ represent, independently of one another, a hydrogen atom, or a linear $C_1$-$C_6$ or branched $C_3$-$C_6$ saturated alkyl group optionally substituted with one or more groups, which may be identical or different, selected from the group consisting of —OH, —$SiMe_3$, —$CO_2R^6$ and —F; or
(ii) $R^1$ and $R^2$ can form, together with the nitrogen atom which bears them, a saturated heterocycle with 5 to 7 ring members and optionally comprising another heteroatom chosen from sulphur and oxygen, this heterocycle being optionally substituted with 1 to 3 linear $C_1$-$C_4$ or branched $C_3$-$C_4$ alkyl group(s) optionally substituted with one or more OH groups;
$R^6$ representing a hydrogen atom or a linear $C_1$-$C_4$ or branched $C_3$-$C_4$ saturated alkyl group;
$R^3$ represents a hydrogen atom;
$R^4$ represents a hydrogen atom or —$OR^4$ represents a phosphate group;
and also the salts, solvates and isomers thereof.
3. The method according to claim 1, wherein in the compound of formula (I):
(i) $R^1$ and $R^2$ represent, independently of one another, a hydrogen atom, or a linear $C_1$-$C_4$ or branched $C_3$-$C_4$ saturated alkyl group optionally substituted with one or more groups, which may be identical or different, selected from the group consisting of —OH, —$SiMe_3$, —$CO_2R^6$ and —F; or
(ii) $R^1$ and $R^2$ can form, together with the nitrogen atom which bears them, a pyrrolidine heterocycle, optionally substituted with one linear $C_1$-$C_4$ or branched $C_3$-$C_4$alkyl group optionally substituted with one or more OH groups;
$R^6$ representing a hydrogen atom or a linear $C_1$-$C_4$, saturated alkyl group;
$R^3$ represents a hydrogen atom;
$R^4$ represents a hydrogen atom or —$OR^4$ represents a phosphate group;
and also the salts, solvates and isomers thereof.
4. The method according to claim 1, wherein in the compound of formula (I):
$R^1$ represents a hydrogen atom, or a linear $C_1$-$C_4$ saturated alkyl group optionally substituted with —OH or —$SiMe_3$;
$R^2$ represents a linear $C_1$-$C_4$ saturated alkyl group substituted with —OH a or $SiMe_3$;
$R^3$ and $R^4$ represent a hydrogen atom.
5. The method according to claim 1, wherein in the compound of formula (I):
$R^1$ represents a linear $C_1$-$C_4$ saturated alkyl group optionally substituted with an —OH group;
$R^2$ represents a linear $C_1$-$C_4$ saturated alkyl group substituted with an —OH group;
$R^3$ and $R^4$ represent a hydrogen atom.
6. The method according to claim 1 wherein the compound of formula (I) is selected from the group consisting of:
(2R,3R)-4-amino-2,3-dihydroxy-4-oxobutyl dihydrogen phosphate;
(2R,3R)-2,3,4-trihydroxy-N,N-dimethylbutanamide;
(2R,3R)-2,3,4-trihydroxybutanamide;
(2R,3R)-N-[bis(trimethylsilyl)methyl]-2,3,4-trihydroxybutanamide;
(2R,3R)-2,3,4-trihydroxy-N-[(trimethylsilyl)methyl]butanamide;
(2R,3R)-2,3,4-trihydroxy-N-(2,2,2-trifluoroethyl)butanamide;
ethyl 4-{[(2R,3R)-2,3,4-trihydroxybutanoyl]amino}butanoate;
4-{[(2R,3R)-2,3,4-trihydroxybutanoyl]amino}butanoic acid;
(2R,3R)-2,3,4-trihydroxy-N-(2-hydroxyethyl)butanamide;
(2R,3R)-N-(2,3-dihydroxypropyl)-2,3,4-trihydroxybutanamide;
(2R,3R)-2,3,4-trihydroxy-N-[2-hydroxy-1,1-bis(hydroxymethyl)ethyl]butanamide;
3-hydroxy-2-{[(2R,3R)-2,3,4-trihydroxybutanoyl]amino}propanoic acid;
(2R,3R)-4-[(2S)-2-(hydroxymethyl)pyrrolidin-1-yl]-4-oxobutane-1,2,3-triol;
(2R,3R)-2,3,4-trihydroxy-N,N-bis(2-hydroxyethyl)butanamide;
(2R,3R)-N-ethyl-2,3,4-trihydroxy-N-(2-hydroxyethyl) butanamide;
methyl [(2,3,4-trihydroxybutanoyl)amino]acetate;
(2R,3R)-4-amino-2,3-dihydroxy-4-oxobutyl disodium phosphate;
(2R,3S)-2,3,4-trihydroxybutanamide;
(2S,3R)-2,3,4-trihydroxybutanamide;
(2R,3S)-4-amino-2,3-dihydroxy-4-oxobutyl disodium phosphate;

(2R,3S)-4-amino-2,3-dihydroxy-4-oxobutyl dihydrogen phosphate; and
(2S,3S)-2,3,4-trihydroxybutanamide.

7. The method according to claim 1 wherein the compound of formula (I) is one selected from the group consisting of:
(2R,3R)-2,3,4-trihydroxybutanamide;
(2R,3R)-2,3,4-trihydroxy-N-[(trimethylsilyl)methyl]butanamide;
(2R,3R)-2,3,4-trihydroxy-N-(2-hydroxyethyl)butanamide;
(2R,3R)-2,3,4-trihydroxy-N,N-bis(2-hydroxyethyl)butanamide; and
(2R,3R)-N-ethyl-2,3,4-trihydroxy-N-(2-hydroxyethyl)butanamide.

8. The method according to claim 1, wherein $R^1$ and $R^2$ together are a saturated heterocycle selected from the group consisting of pyrrolidine, piperidine, morpholine, thiomorpholine and cyclohexamethyleneimine.

9. The method according to claim 1, wherein $R^1$ and $R^2$ together are a saturated heterocycle selected from the group consisting of pyrrolidine.

10. The method according to claim 2, wherein $R^1$ and $R^2$ together are a saturated heterocycle selected from the group consisting of pyrrolidine, piperidine, morpholine, thiomorpholine and cyclohexamethyleneimine.

11. The method according to claim 2, wherein $R^1$ and $R^2$ together are a saturated heterocycle selected from the group consisting of pyrrolidine.

12. The method according to claim 1, wherein $R^1$ and $R^2$ together are a pyrrolidine heterocycle-substituted with a hydroxymethyl group.

13. The method according to claim 1, wherein $R^6$ is a linear ($C_1$-$C_2$) saturated alkyl group.

14. The method according to claim 1, wherein $R^4$ is a hydrogen atom.

15. The method according to claim 1, wherein $R^1$ is a linear $C_1$-$C_2$ saturated alkyl group optionally substituted with —OH or —SiMe$_3$.

16. The method according to claim 1, wherein $R^2$ represents a linear $C_1$-$C_2$ saturated alkyl group substituted with —OH or SiMe$_3$.

17. The method according to claim 1, wherein $R^1$ represents a linear $C_1$-$C_2$ saturated alkyl group optionally substituted with an —OH group.

18. The method according to claim 1, wherein $R^2$ represents a linear $C_1$-$C_2$ saturated alkyl group substituted with an —OH group.

19. The method according to claim 1, wherein $R^1$ is a hydrogen atom.

20. The method according to claim 1, wherein in the compound of formula (I):
$R^1$ is a hydrogen atom;
$R^2$ represents a linear $C_1$-$C_4$ saturated alkyl group substituted with an —OH group;
$R^3$ and $R^4$ represent a hydrogen atom.

* * * * *